(12) United States Patent
Tada

(10) Patent No.: US 9,953,409 B2
(45) Date of Patent: Apr. 24, 2018

(54) TIRE INSPECTION METHOD AND DEVICE THEREFOR

(71) Applicant: The Yokohama Rubber Co., LTD., Minato-ku, Tokyo (JP)

(72) Inventor: Hirotaro Tada, Hiratsuka (JP)

(73) Assignee: The Yokohama Rubber Co., LTD. (JP)

( * ) Notice: Subject to any disclaimer, the term of this patent is extended or adjusted under 35 U.S.C. 154(b) by 6 days.

(21) Appl. No.: 15/101,573

(22) PCT Filed: Nov. 28, 2014

(86) PCT No.: PCT/JP2014/081585
§ 371 (c)(1),
(2) Date: Jun. 3, 2016

(87) PCT Pub. No.: WO2015/083643
PCT Pub. Date: Jun. 11, 2015

(65) Prior Publication Data
US 2016/0307313 A1    Oct. 20, 2016

(30) Foreign Application Priority Data

Dec. 3, 2013   (JP) ................................ 2013-249930

(51) Int. Cl.
*G06K 9/00*    (2006.01)
*G06K 9/46*    (2006.01)
(Continued)

(52) U.S. Cl.
CPC .......... *G06T 7/0006* (2013.01); *B60C 25/002* (2013.01); *B60C 25/0554* (2013.01);
(Continued)

(58) Field of Classification Search
None
See application file for complete search history.

(56) References Cited

U.S. PATENT DOCUMENTS

| 4,857,749 A | 8/1989 | McCarty |
| 5,083,306 A * | 1/1992 | Steffel ................. G01M 17/028 |
| | | 378/207 |

(Continued)

FOREIGN PATENT DOCUMENTS

| JP | H09-015172 | 1/1997 |
| JP | 2001-004561 | 1/2001 |

(Continued)

OTHER PUBLICATIONS

International Search Report for International Application No. PCT/JP2014/081585 dated Feb. 24, 2015, 2 pages, Japan.

*Primary Examiner* — Randolph I Chu
(74) *Attorney, Agent, or Firm* — Thorpe North & Western

(57) ABSTRACT

A tire inspection method includes: capturing a transmission image of a tire including a steel chafer at a bead portion; generating an image at an inspection device from the captured image of a full revolution of the tire with the steel chafer portions extracted using a spatial filter generated in accordance with an incline of the wires of the steel chafer; detecting a locus of a front side edge and a back side edge of the steel chafer; generating an image from the captured image with the steel chafer portions removed; detecting a locus of a turned-up edge of a carcass from this image; and determining at the inspection device the position of the carcass to be appropriate or not on the basis of the locus of the turned-up edge of the carcass.

20 Claims, 14 Drawing Sheets

(51) Int. Cl.
　　　*G06K 9/66*　　　(2006.01)
　　　*G06T 7/00*　　　(2017.01)
　　　*B60C 99/00*　　　(2006.01)
　　　*B60C 25/00*　　　(2006.01)
　　　*B60C 25/05*　　　(2006.01)
　　　*G06T 7/73*　　　(2017.01)
　　　*G01N 23/18*　　　(2018.01)
　　　*B60C 15/00*　　　(2006.01)
　　　*B60C 15/06*　　　(2006.01)

(52) U.S. Cl.
　　　CPC ........... *B60C 99/00* (2013.01); *G01N 23/185* (2013.01); *G06T 7/73* (2017.01); *B60C 15/0009* (2013.01); *B60C 15/0635* (2013.01); *G06T 2207/20056* (2013.01); *G06T 2207/30252* (2013.01)

(56)　　　　　　References Cited

U.S. PATENT DOCUMENTS

| 5,737,383 | A | * | 4/1998 | Noda | ................. | G01M 17/028 |
|---|---|---|---|---|---|---|
| | | | | | | 378/57 |
| 8,087,301 | B2 | * | 1/2012 | Hammerschmidt | .. | G06T 7/0004 |
| | | | | | | 382/141 |

FOREIGN PATENT DOCUMENTS

| JP | 2013-159279 | 8/2013 |
|---|---|---|
| JP | 2013-217712 | 10/2013 |

* cited by examiner

IMAGE WITH STEEL CHAFER REMOVED

COMPRESSED IMAGE OF FULL REVOLUTION OF TIRE

CAPTURED IMAGE

COMPRESSED IMAGE OF FULL REVOLUTION OF TIRE

TIRE INSPECTION METHOD AND DEVICE THEREFOR

TECHNICAL FIELD

The present technology relates to a tire inspection method of inspecting for acceptability of the position of a turned-up edge of a carcass using a transmission electromagnetic wave image taken by irradiating a tire with electromagnetic waves, and a device therefor.

BACKGROUND ART

Conventional methods of inspecting a tire for acceptability of the position of a turned-up edge of a carcass using a transmission electromagnetic wave image taken by irradiating the tire with electromagnetic waves include a method of:

rotating the tire in the circumferential direction while irradiating the tire with X-rays from the inner circumferential surface side of the tire toward the tire, and taking a transmission X-ray image of the tire via an image capture device disposed to the outer circumferential surface side of the tire. Additionally, the captured image is displayed on a display device, and an inspector visually determines the state of the belt cords and the like in the image displayed on the display device.

Another known tire inspection method (see, for example, Japanese Unexamined Patent Application Publication No. H09-15172 A) includes:

taking a transmission X-ray image using an image capture device in a similar manner to that described above, comparing the captured image with pre-stored reference data, and determining the state of the belt cords and the like on the basis of the differences between the reference data and the captured image.

However, the inspection methods described above include an inspector visually determining the state of the belt cords and the like. As such, the accuracy of determination is difficult to improve, and means to reduce the time needed for the inspection are difficult to come by.

Furthermore, in the case of inspecting for acceptability of the position of a turned-up edge of a carcass, a steel chafer is disposed enclosing the turned-up portion. Thus, in the captured image, the edges of the steel chafer and the turned-up portion of the carcass are in close proximity to one another. Consequently, the turned-up edge of the carcass is difficult to distinguish via visual inspection by an inspector, leading to cases in which an extended period of time is needed for the inspection.

SUMMARY

The present technology provides a tire inspection method that enables efficient and highly accurate inspection of the position of a turned-up edge of a carcass of a tire and the position of an edge of a reinforcing member of the tire such as a steel chafer and a device therefor.

The present technology includes the various embodiments described below.

First Embodiment

A tire inspection method comprising the steps of:

performing two dimension Fourier transformation on a captured transmission electromagnetic wave image obtained from electromagnetic waves transmitting through:

a first region in a tire in which a plurality of reinforcing wires disposed in a reinforcing layer of the tire extends from first ends of the reinforcing wires at an incline in a first direction with respect to a tire width direction, and a second region in the tire in which the reinforcing wires extend at an incline in a second direction different from the first direction due to the reinforcing layer being turned up;

extracting a first image component including the first ends of the reinforcing wires located in the first region from a process result of the two dimension Fourier transformation using a first spatial filter generated in accordance with the incline in the first direction;

acquiring a first processed image including the first ends located in the first region by performing inverse two dimension Fourier transformation on an extraction result of the first image component;

identifying positions of the first ends in the captured image using the first processed image; and inspecting a position of an edge of the reinforcing layer in the tire on the basis of the positions of the first ends.

Second Embodiment

The tire inspection method according to the first embodiment, wherein the reinforcing wires include second ends located in the second region; and further comprising the steps of:

extracting a second image component including the second ends of the reinforcing wires located in the second region from a process result of the two dimension Fourier transformation using a second spatial filter generated in accordance with the incline in the second direction, acquiring a second processed image including the second ends located in the second region by performing inverse two dimension Fourier transformation on an extraction result of the second image component, and identifying positions of the second ends in the captured image using the second processed image, wherein upon inspection, a position of an edge of the reinforcing layer in the tire is inspected on the basis of the positions of the second ends and the first ends.

Third Embodiment

The tire inspection method according to the first or second embodiment wherein the tire comprises a layer-like skeleton member including a plurality of tire skeleton wires disposed in the first region and the second region, the tire skeleton wires extending in a third direction different from the first direction and the second direction and including third ends located in the first region;

the captured image includes images of the reinforcing wires and the skeleton wires; and further comprising the steps of:

generating a working image from the captured image by removing the images of the reinforcing wires located in the first region using the captured image and the first processed image, identifying positions of the third ends of the skeleton wires in the captured image using the working image, and inspecting a position of an edge of the skeleton member in the tire on the basis of the identified positions of the third ends.

Fourth Embodiment

The tire inspection method according to second embodiment, wherein
the tire comprises a layer-like skeleton member including a plurality of tire skeleton wires disposed in the first region and the second region, the tire skeleton wires extending in a third direction different from the first direction and the second direction and including third ends located in the first region;
the captured image includes images of the reinforcing wires and the skeleton wires; and further comprising the steps of:
generating a working image from the captured image by removing the images of the reinforcing wires located in the first region and the second region using the captured image, the first processed image, and the second processed image,
identifying positions of the third ends of the skeleton wires in the captured image using the working image, and
inspecting a position of an edge of the skeleton member on the basis of the identified positions of the third ends.

Fifth Embodiment

The tire inspection method according to the third or fourth embodiment, wherein the positions of the third ends are identified on the basis of an image generated by performing dynamic binarization processing on the working image.

Sixth Embodiment

The tire inspection method according to any one of third to fifth embodiments, wherein
the position of the edge of the skeleton member is inspected all around in a tire circumferential direction, and
if the positions of the third ends are closer to a turned-up position of the reinforcing wires than the position of the first ends at all locations in the tire circumferential direction, the position of the edge of the skeleton member in the tire is determined to be appropriate.

Seventh Embodiment

The tire inspection method according to any one of third to sixth embodiments, wherein
the position of the edge of the skeleton member is inspected all around in the tire circumferential direction, and
if the positions of the third ends are between the positions of the first ends and the positions of the second ends at all locations in the tire circumferential direction, the position of the edge of the skeleton member in the tire is determined to be appropriate.

Eighth Embodiment

The tire inspection method according to any one of the third to seventh embodiments, wherein the positions of the first ends, the second ends, and the third ends are identified as positions on corresponding loci of a full revolution of the tire along the tire circumferential direction.

Ninth Embodiment

The tire inspection method according to any one of the third to seventh embodiments, further comprising the step of:
displaying a composite image of:
an image of a full revolution in the tire circumferential direction of the captured image compressed in the tire circumferential direction, and
loci in a full revolution of the tire of the positions of the first ends of the reinforcing wires, positions of the second ends of the reinforcing wires, and the positions of the third ends of the skeleton wires.

Tenth Embodiment

The tire inspection method according to any one of the first to ninth embodiments, further comprising the step of displaying the captured image.

Eleventh Embodiment

The tire inspection method according to any one of the first to tenth embodiments, wherein the reinforcing layer is a steel chafer disposed at a bead portion, the steel chafer including steel cords.

Twelfth Embodiment

The tire inspection method according to any one of the third to ninth embodiments, wherein the skeleton member is a carcass turned up at the bead portion.

Thirteenth Embodiment

A tire inspection device comprising:
a two dimension Fourier transformation unit configured to perform two dimension Fourier transformation on a captured transmission electromagnetic image obtained from electromagnetic waves transmitting through:
a first region in a tire in which a plurality of reinforcing wires disposed in a reinforcing layer of the tire extends from first ends of the reinforcing wires at an incline in a first direction with respect to a tire width direction, and
a second region in the tire in which the reinforcing wires extend at an incline in a second direction different from the first direction due to the reinforcing layer being turned up;
a processed image acquisition unit configured to
extract a first image component including the first ends of the reinforcing wires located in the first region from a process result of the two dimension Fourier transformation using a first spatial filter generated in accordance with the incline in the first direction, to
acquire a first processed image including the first ends located in the first region by performing inverse two dimension Fourier transformation on an extraction result of the first image component;
an edge extraction unit configured to identify positions of the first ends in the captured image using the first processed image; and
an inspection unit configured to inspect a position of an edge of the reinforcing layer in the tire on the basis of the positions of the first ends.

Fourteenth Embodiment

The tire inspection device according to the thirteenth embodiment, wherein
the reinforcing wires include second ends located in the second region;
the processed image acquisition unit is configured to
extract a second image component including the second ends of the reinforcing wires located in the second region from a process result of the two dimension Fourier transformation using a second spatial filter generated in accordance with the incline in the second direction of the reinforcing wires, to acquire a second processed image including the second ends located in the second region by performing inverse two dimension Fourier transformation on an extraction result of the second image component;

the edge extraction unit is configured to identify positions of the second ends in the captured image using the second processed image; and the inspection unit is configured to inspect a position of an edge of the reinforcing layer in the tire on the basis of the positions of the second ends and the first ends.

Fifteenth Embodiment

The tire inspection device according to the thirteenth or fourteenth embodiment, wherein the tire comprises a layer-like skeleton member including a plurality of tire skeleton wires disposed in the first region and the second region, the tire skeleton wires extending in a third direction different from the first direction and the second direction and including third ends located in the first region;

the captured image includes images of the reinforcing wires and the skeleton wires;

the tire inspection device comprises a working image generation unit configured to generate a working image from the captured image by removing the images of the reinforcing wires located in the first region using the captured image and the first processed image;

the edge extraction unit is configured to identify positions of the third ends of the skeleton wires in the captured image using the working image; and the inspection unit is configured to inspect a position of an edge of the skeleton member in the tire on the basis of the identified positions of the third ends.

Sixteenth Embodiment

The tire inspection device according to the thirteenth or fourteenth embodiment, wherein the tire comprises a layer-like skeleton member including a plurality of tire skeleton wires disposed in the first region and the second region, the tire skeleton wires extending in a third direction different from the first direction and the second direction and including third ends located in the first region;

the captured image includes images of the reinforcing wires and the skeleton wires;

the tire inspection device comprises a working image generation unit configured to generate a working image from the captured image by removing the images of the reinforcing wires located in the first region and the second region using the captured image, the first processed image, and the second processed image;

the edge extraction unit is configured to identify positions of the third ends of the skeleton wires in the captured image using the working image; and the inspection unit is configured to inspect a position of an edge of the skeleton member in the tire on the basis of the identified positions of the third ends.

Seventeenth Embodiment

The tire inspection device according to the fifteenth or sixteenth embodiment, further comprising:

a binarization unit configured to perform dynamic binarization processing on the working image, and wherein the edge extraction unit is configured to identify the positions of the third ends on the basis of the working image on which the dynamic binarization processing is performed.

Eighteenth Embodiment

The tire inspection device according to any one of the fifteenth to seventeenth embodiments, wherein the inspection unit determines the position of the edge of the skeleton member in the tire to be appropriate if the positions of the third ends are closer to a turned-up position of the reinforcing wires than the positions of the first ends at all locations in the tire circumferential direction.

Nineteenth Embodiment

The tire inspection device according to any one of the fifteenth to eighteenth embodiments, wherein the inspection unit determines the position of the edge of the skeleton member in the tire to be appropriate if the positions of the third ends are between the positions of the first ends and the positions of the second ends at all locations in the tire circumferential direction.

Twentieth Embodiment

The tire inspection device according to any one of the fifteenth to seventeenth embodiments, wherein the edge extraction unit identifies the positions of the first ends, the second ends, and the third ends as positions on corresponding loci of a full revolution of the tire along the tire circumferential direction.

Twenty-First Embodiment

The tire inspection device according to any one of the fifteenth to twentieth embodiments, further comprising a display unit configured to display a composite image of:

an image of a full revolution in the tire circumferential direction of the captured image compressed in the tire circumferential direction, and loci in a full revolution of the tire of the positions of the first ends of the reinforcing wires, the positions of the second ends of the reinforcing wires, and the positions of the third ends of the skeleton wires.

Twenty-Second Embodiment

The tire inspection device according to any one of the fifteenth to twentieth embodiments, further comprising a display unit configured to display the captured image.

Specifically, the tire inspection method described above uses the inspection device, and the electromagnetic wave irradiation device and the image capture device disposed on either side of the bead portions of the tire for inspection. Electromagnetic waves such as X-rays or gamma rays are irradiated from the electromagnetic wave irradiation device toward the bead portions and the image capture device captures a transmission electromagnetic wave image of that which transmitted through the bead portions. The inspection device uses this captured image to inspect around the full revolution of the tire whether or not the position of the turned-up edge of the carcass at the bead portions are appropriate.

The inspection device performs two dimension Fourier transformation on the image captured by the image capture device, extracts from the result of the two dimension Fourier transformation the portions of the steel chafer disposed turned-up enclosing the turned-up portion of the carcass, acquires an image of the portion including the ends of the steel chafer by performing inverse two dimension Fourier transformation on the extraction result, and detects the locus of the ends of the steel chafer from this image. Additionally, the inspection device extracts from the result of the two dimension Fourier transformation portions including the other ends of the steel chafer, acquires an image of portions including the other ends of the steel chafer by performing inverse two dimension Fourier transformation on the extraction result, and detects the locus of the other ends of the steel chafer from this image. The inspection device also generates a working image with the steel chafer portions removed from the image captured by the image capture device, performs dynamic binarization processing on the working image, extracts the locus of the turned-up edge of the carcass from the binarization processed image, and determines whether or not the extracted position of the turned-up edge of the carcass is appropriate.

The tire inspection device described above irradiates electromagnetic waves such as X-rays or gamma rays from the electromagnetic wave irradiation device disposed on one side of the bead portions of the tire for inspection toward the bead portions. The image capture device captures a transmission electromagnetic wave image of that which transmitted through the bead portions and uses this captured image to inspect around the full revolution of the tire whether or not the position of the turned-up edge of the carcass at the bead portions are appropriate.

The inspection device comprises:

a two dimension Fourier transformation means configured to perform two dimension Fourier transformation on the image captured by the image capture device;

a first image acquisition means configured to extract from the two dimension Fourier transformation result first end portions of the steel chafer, the steel chafer being disposed turned-up enclosing the turned-up portion of the carcass, and acquire an image of first end portions of the steel chafer by performing inverse two dimension Fourier transformation on the extracted result;

a first edge extraction means configured to extract the locus of the first end side edge of the steel chafer from the image captured by the first image acquisition means;

a second image acquisition means configured to extract from the two dimension Fourier transformation result second end side portions of the steel chafer, and acquire an image of the second end side portions of the steel chafer by performing inverse two dimension Fourier transformation on the extracted result;

a second edge extraction means configured to extract the locus of the second end side edge of the steel chafer from the image captured by the second image acquisition means;

a working image generation means configured to generate a working image with the steel chafer portions removed from the image captured by the image capture device;

a binarization means configured to perform binarization processing on the working image;

a turned-up edge extraction means configured to extract a locus of the turned-up edge of the carcass from the binarization processed image; and a determination means configured to determine whether or not the extracted position of the turned-up edge is appropriate.

The tire inspection method and device therefor of the present technology can extract only the reinforcing wires from the captured image of the tire including the reinforcing wires using a spatial filter generated in accordance with the incline of the reinforcing wires with respect to the tire width direction, accurately determine the positions of the ends of the reinforcing wires, and efficiently inspect the arrangement of the reinforcing wires in the tire.

Additionally, according to the tire inspection method and device therefor, when the arrangement of the skeleton wires used in the carcass and the like is inspected using the image of a full revolution of the tire, the position of the edge or locus of the reinforcing wires of the steel chafer and the like and the position of the edge or locus of the skeleton wires of the carcass turned-up edge and the like can be automatically extracted. As a result, the determination of whether or not the arrangement of the skeleton wires are appropriate, including whether or not there are carcass turned-up defects, can be performed with greater accuracy and in a shorter time than if performed by an inspector and 100% reproducibility and repeatability is possible. In addition, because visual observation of the displayed image by an inspector becomes unnecessary, when the tire is rotated for image capturing, the tire rotation speed can be set high, thus shortening the inspection time.

DETAILED DESCRIPTION

Embodiments of the present technology are described below with reference to the drawings.

Figure 1:
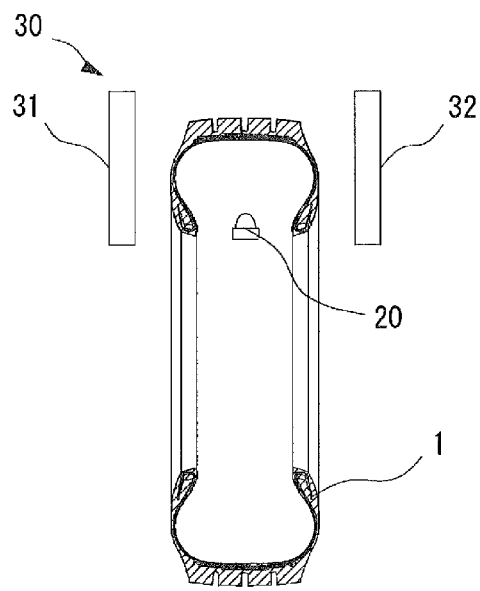
FIG. 1 is a schematic view of an irradiation device and an image capture device according to an embodiment of the present technology.
Figure 2:
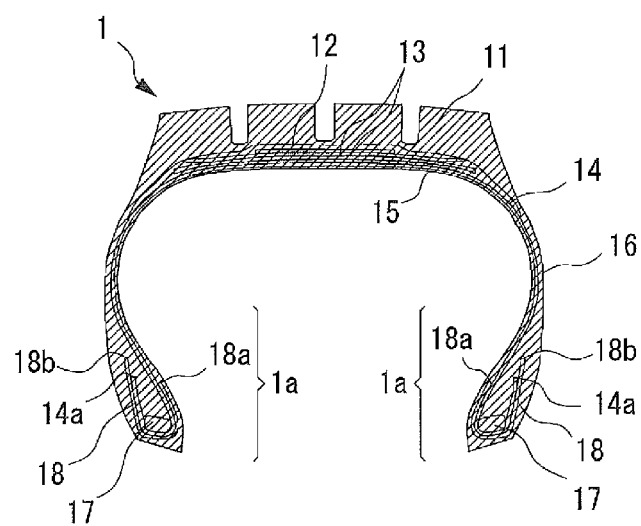
FIG. 2 is a cross-sectional view illustrating main components of a tire for inspection according to an embodiment of the present technology.
Figure 3:
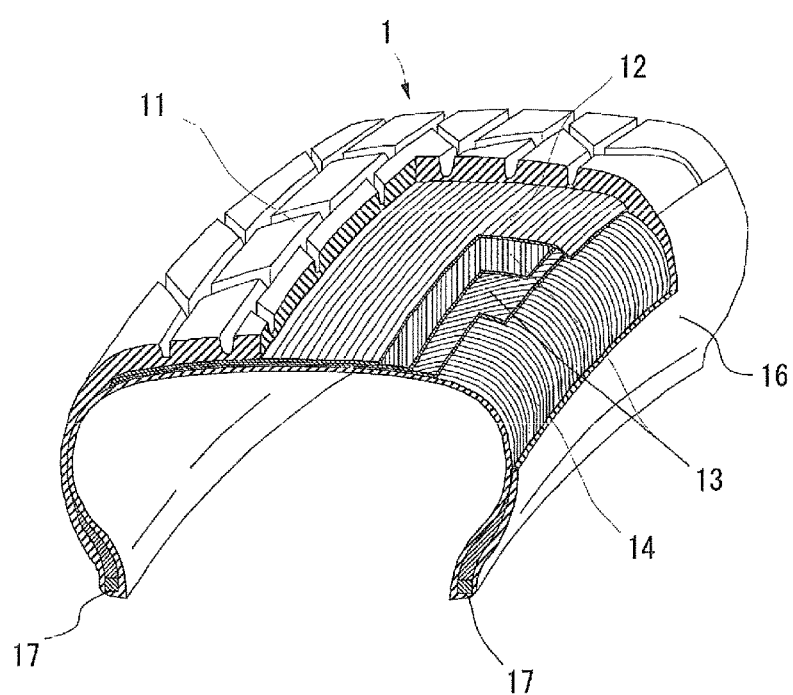
FIG. 3 is a partially broken perspective view illustrating main components of a tire for inspection according to an embodiment of the present technology.
Figure 4:
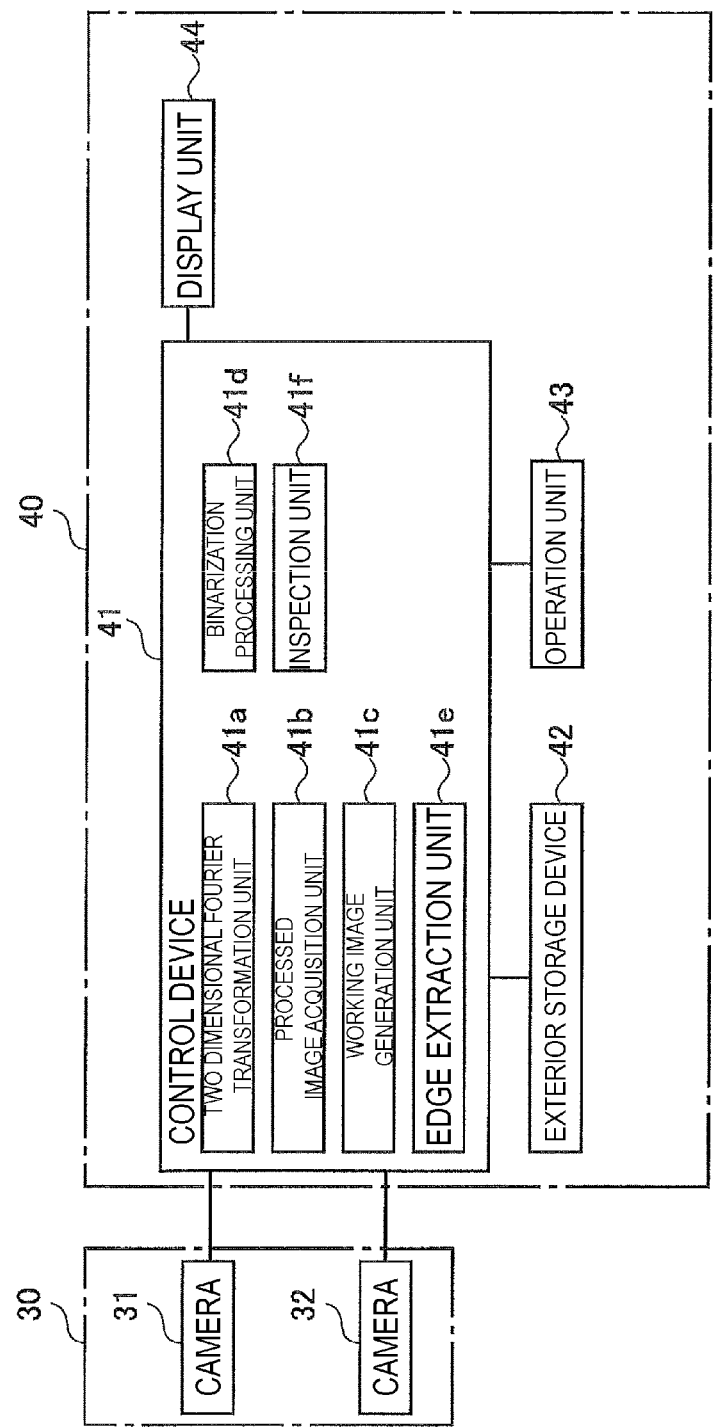
FIG. 4 is a block diagram illustrating an electrical circuit of a tire inspection device according to an embodiment of the present technology.

FIG. 1 is a schematic view of an irradiation device and an image capture device according to an embodiment of the present technology. FIG. 2 is a cross-sectional view of main components of a tire for inspection according to an embodiment of the present technology. FIG. 3 is a partially broken perspective view of main components of a tire for inspection according to an embodiment of the present technology. FIG. 4 is a block diagram of an electrical circuit of a tire inspection device according to an embodiment of the present technology.

The tire inspection device of the present embodiment is provided with an irradiation device 20, an image capture device 30, and an inspection device main body 40.

The irradiation device 20 is disposed inward of the inner circumferential surface of the tire 1 and irradiates X-rays toward the tire 1.

The image capture device 30 is disposed outward of the outer side surface of the tire 1 and captures a transmission X-ray image of a bead portion 1a of the tire 1.

The inspection device main body 40 is connected to the image capture device 30 and inspects the arrangement of internal components of the tire 1 such as a carcass or a steel chafer in the bead portion 1a using imaging, i.e., a transmission electromagnetic wave image. The tire 1 is supported in a manner allowing the tire 1 to freely rotate by a support device (not illustrated).

The tire 1 is, for example, a known tubeless radial tire and includes known components such as a cap tread 11, an undertread 12, belts 13, a carcass 14, an innerliner 15, and sidewalls 16. Each end portion of the carcass 14 in the tire width direction is turned up at a bead 17 from the inward side to the outward side, i.e., from the side of the air-filled tire cavity region covered by the tire and the rim to the side on which the tire comes into contact with the atmosphere, also from the inner side in the tire radial direction to the outer side in the tire radial direction. The tire 1 additionally includes steel chafers 18 covering these carcass end portions. The side of the tire cavity region is referred to as "inner side" or "back side". The side on which the tire comes into contact with the atmosphere is referred to as "outer side" or "front side". In the target tire structure, a carcass turned-up edge 14a is stipulated to be disposed at a position above that of an inner side edge 18a of the steel chafer 18 located at the inner side of the tire (see FIG. 2). In addition, the carcass turned-up edge 14a is preferably disposed at a position above that of the inner side edge 18a of the steel chafer 18 located at the inner side of the tire (see FIG. 2), in other words located further to the outer side in the tire radial direction, and below an outer side edge 18b of the steel chafer 18 (see FIG. 2), in other words further to the inner side in the tire radial direction.

The carcass 14 of the tire 1 includes a plurality of metal carcass cords extending in the tire radial direction. A tire structure including a steel chafer 18 such as that of tire 1 according to the present embodiment is capable of suppressing separation at the bead 17 and carcass turned-up portion.

The irradiation device 20 includes a known X-ray tube that irradiates X-rays in a radial manner and is disposed inward of the inner circumferential surface of the tire 1 supported by the support device. Note that a configuration in which gamma rays are irradiated instead of X-rays is also possible.

The image capture device 30 includes a pair of side cameras 31, 32 disposed on either side of the tire 1 in the width direction, the tire 1 being supported by the support device. Each camera 31, 32 is constituted by a known line sensor camera that captures a transmission X-ray image of the tire 1 as an image line. Specifically, the cameras 31, 32 capture images at intervals of a predetermined period of time while the tire 1 is in a state of being rotated in the tire circumferential direction at a predetermined speed by the support device, thus capturing transmission X-ray images of a full revolution of the tire 1.

The inspection device main body 40, as illustrated in FIG. 4, is provided with a control device 41 constituted by a known computer device; an exterior storage device 42 connected to the control device 41; an operation unit 43, which includes a mouse, keyboard, and the like, connected to the control device 41; and a display unit 44, which includes a liquid crystal display.

In the tire inspection device configured as described above, the cameras 31, 32 capture images at intervals of a predetermined period of time while the tire 1 is in a state of being rotated in the tire circumferential direction at a predetermined speed by the support device (not illustrated), thus capturing transmission X-ray images of a full revolution of the tire 1. The images captured by the camera 31 and the images captured by the camera 32 are input to the control device 41 as digital images. Note that the line image data captured by the cameras 31, 32 can be compiled at the control device 41 to generate an image of a full revolution of the tire 1.

Figure 5:
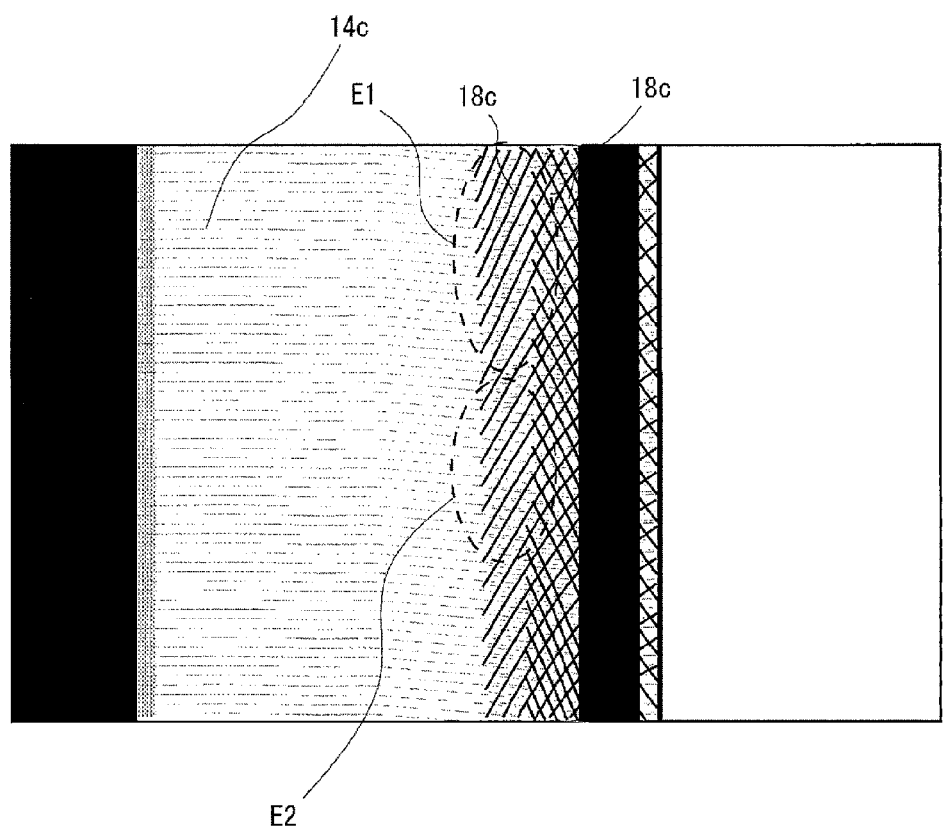
FIG. 5 is a diagram for explaining a captured image of a tire according to an embodiment of the present technology.

Here, an image of a full revolution of the tire 1, which is inputted to the control device 41, is an image of the tire 1 taken from the outer side of the tire 1. In this image, as illustrated in FIG. 5, the image of the turned-up portion of the carcass 14, and the image of the steel chafer 18 and the bead 17 are visible. Within the image of the carcass 14, the plurality of metal carcass cords 14c that constitute the carcass layer are visible; and within the image of the steel chafer 18, a plurality of steel cords 18c that constitute the steel chafer 18 are visible.

The images of the carcass cords 14c are arranged extending in the width direction of the image with intervals between one another in the vertical direction of the image. The images of the steel cords 18c that constitute the steel chafer 18 have a predetermined angle with respect to the width direction of the image and are arranged with intervals between one another in the vertical direction of the image. Thus, the angle at which the steel cords 18c are disposed at the inner surface side and the angle at which the steel cords 18c are disposed at the outer surface side are different.

When the images of carcass cords 14c on the back side fall in the gaps between the images of the carcass cords 14c on the front side, as seen in region E1 of FIG. 5, the images of the carcass turned-up edge in this perspective image can be visually observed. However, when the images of the carcass cords 14c on the front side and the images of the carcass cords 14c on the back side overlap, as seen in region E2 of FIG. 5, the images of the carcass turned-up edge in this perspective image cannot be visually observed. The inspection device according to the present embodiment is capable of identifying the position of the carcass turned-up edge even when the images of the carcass cords 14c on the front side and back side overlap.

Hereinafter, the operation of the inspection device main body 40 according to the present embodiment will be described with reference to the flowcharts illustrated in FIGS. 6 to 8. In the present embodiment, image processing of the image of a full revolution of the tire 1 and determination of the acceptability of the position of the carcass turned-up edge is performed by the control device 41 on the basis of the processed image.

The control device 41 of the inspection device main body 40 includes a two dimensional Fourier transformation unit 41a, a processed image acquisition unit 41b, a working image generation unit 41c, a binarization processing unit 41d, an edge extraction unit 41e, and an inspection unit 41f. The two dimensional Fourier transformation unit 41a, the processed image acquisition unit 41b, the working image generation unit 41c, the binarization processing unit 41d, the edge extraction unit 41e, and the inspection unit 41f are software modules generated by the activation of a program by a computer. The operation of each of these units will be described as part of the description of the operation of the inspection device main body 40 below.

Figure 6:
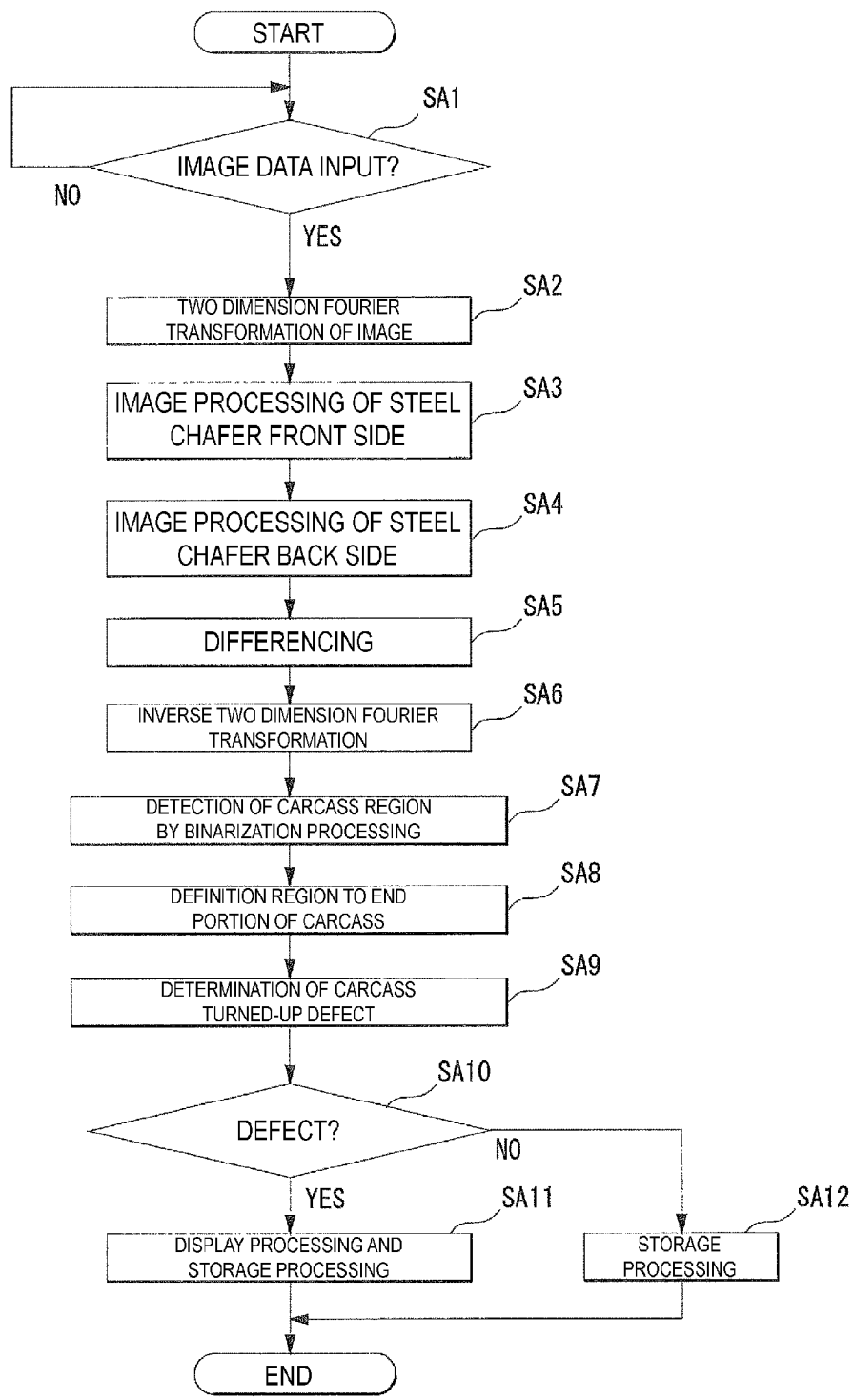
FIG. 6 is a flowchart for explaining the operation of the inspection device according to an embodiment of the present technology.
Figure 9:
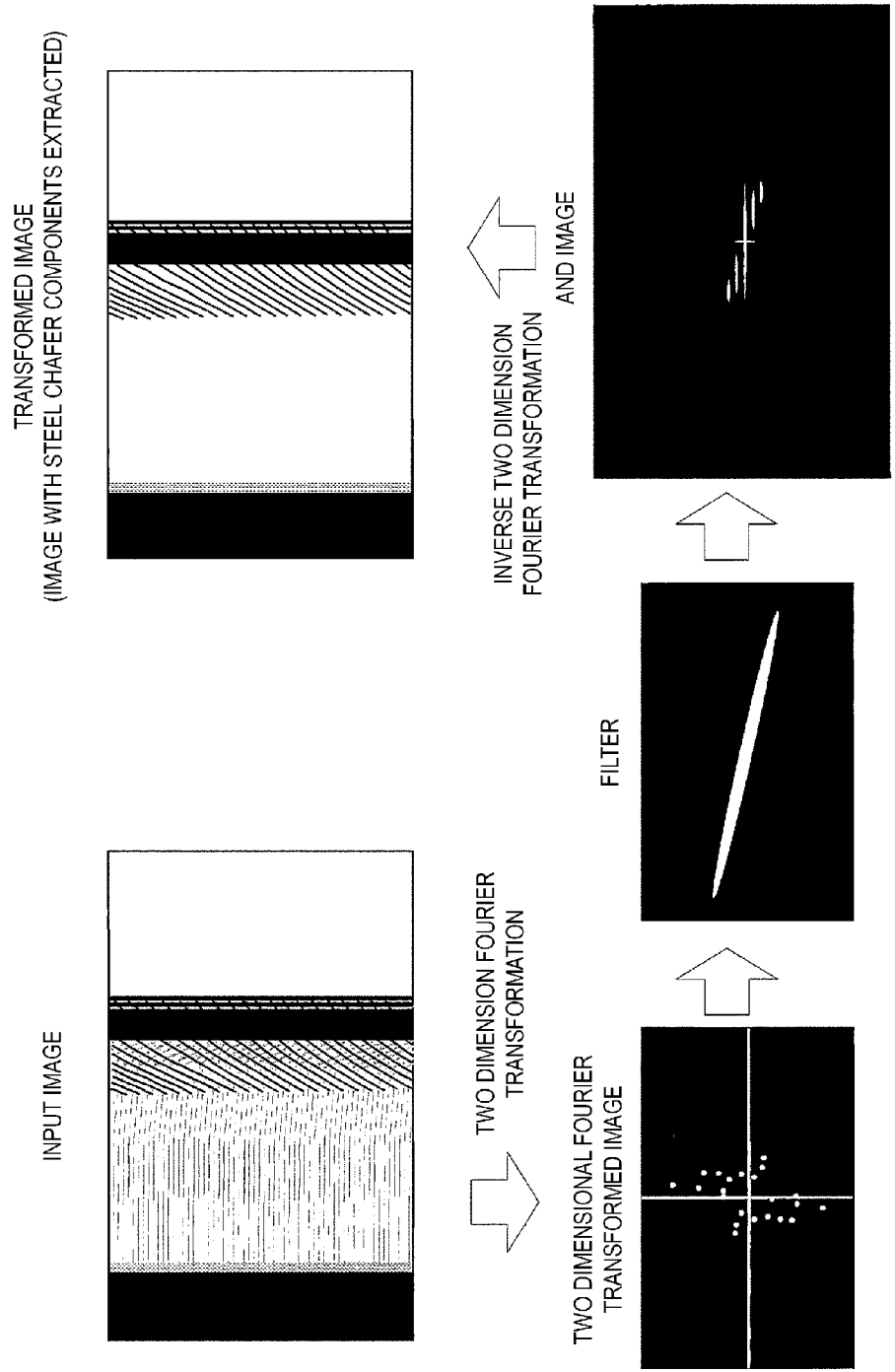
FIG. 9 is a diagram for explaining the steps involved in the image processing of extracting steel chafer components according to an embodiment of the present technology.

When operation of the inspection device main body 40 starts, the control device 41 determines whether or not image data from the cameras 31, 32 has been input (SA1), as illustrated in the flowchart of FIG. 6. If image data has been input, the two dimensional Fourier transformation unit 41a of the control device 41 performs two dimensional Fourier transformation on the input image (the captured transmission electromagnetic wave image) and generates a two dimensional Fourier transformed image (SA2), as illustrated in FIG. 9. Next, the processed image acquisition unit 41b of the control device 41 performs image processing on the front side of the steel chafer 18 located at the front side (tire front surface side) (SA3).

Figure 7:
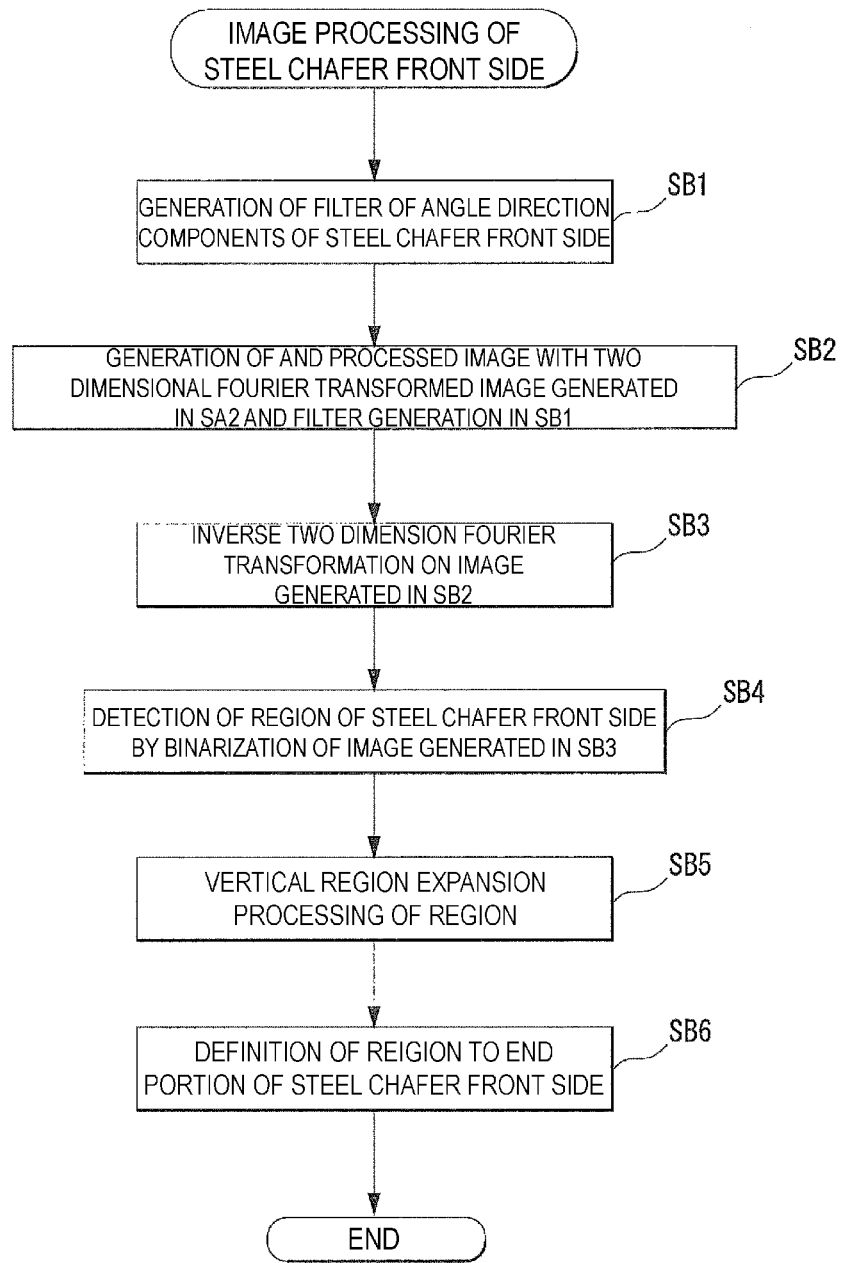
FIG. 7 is a flowchart for explaining the operation of the inspection device according to an embodiment of the present technology.

The image processing of the front side of the steel chafer 18 performed by the processed image acquisition unit 41b includes generating a spatial filter to extract only the steel cords angle direction components of the steel chafer 18 located at the front side (SB1), as illustrated in FIG. 7. The processed image acquisition unit 41b performs an AND process with the two dimensional Fourier transformed image generated in the SA2 processing described above and the spatial filter generated in the SB1 processing described above and generates an AND image (SB2). The AND process is a process of multiplying the data value (gradation value) of each pixel of the two dimensional Fourier transformed image by the filter coefficient of the position corresponding to each pixel the spatial filter is applied to. In such a manner, an image component including the ends of the steel cords 18c is extracted from the two dimension Fourier transformation process result using a spatial filter. Additionally, the processed image acquisition unit 41b performs inverse two dimension Fourier transformation of the AND image generated in the SB2 processing and generates a transformed image (SB3). This transformed image is an image in which images of the steel cords 18c of the steel chafer located at the front side are clearly shown. In other words, a processed image including the ends of the steel cords 18c of the steel chafer 18 located at the front side is acquired. Note that for generating the spatial filter to extract only the steel cords angle direction components of the steel chafer 18 located at the front side in the SB1 processing described above, the angle of the steel cords are found by an inspector beforehand and the value is input into the control device 41 via the operation unit 43. In other words, the spatial filter is generated in accordance with the incline of the steel cords 18c of the steel chafer 18. Accordingly, the images of the steel cords 18c before being turned up at the bead portion 1a having one angle of inclination and the steel cords 18c after being turned up at the bead portion 1a having a different angle of inclination are separable via the spatial filter.

Figure 10:
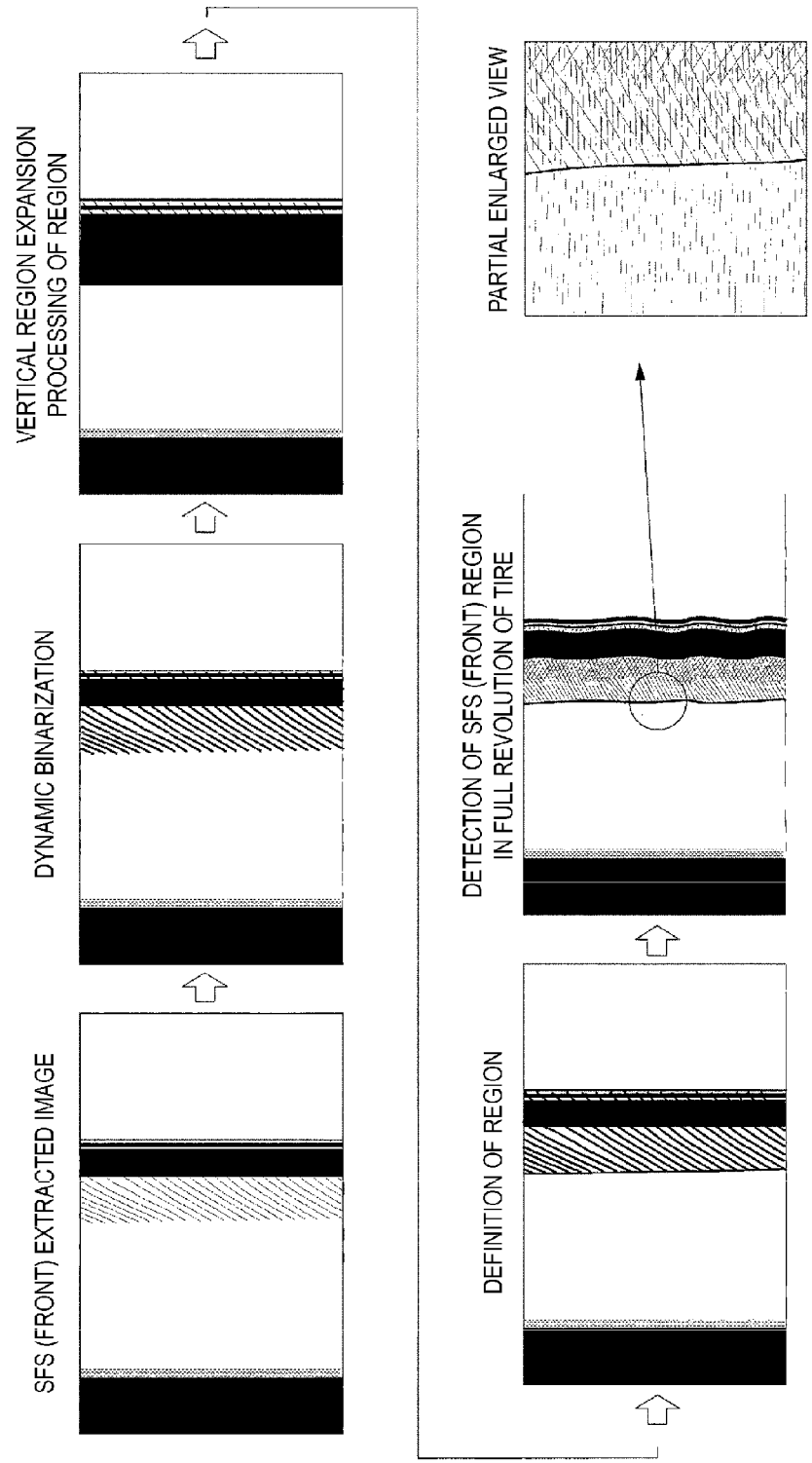
FIG. 10 is a diagram for explaining the steps involved in the image processing of detecting a front side edge of a steel chafer according to an embodiment of the present technology.

Next, the binarization processing unit 41d of the control device 41, as illustrated in FIG. 10, performs known dynamic binarization processing on the transformed image generated in the SB3 processing and detects the region of the steel chafer 18 located at the front side (SB4) and performs vertical region expansion processing (SB5). Dynamic binarization processing refers to binarization processing in which the transformed image is divided into regions of a predetermined size, for example, regions of 15×15 pixels, and the average value of the data value (gradation value) of the pixels in each region is used to determine the threshold value for binarization of the corresponding region. In the case of an 8 bit gradation, the data value (gradation value) of each pixel is set to either 0 or 255 according to the threshold value. The threshold value is set independently for each region, thus when the average value described above differs between regions, so does the threshold value. The threshold value described above may be the average value of the data value of each region, may be the sum or difference of the average value and a certain value, or may be the product of the average value and a certain value. In the present embodiment, dynamic binarization processing is performed. However, typical binarization processing using a fixed threshold value without dividing the image into regions may be employed. Vertical region expansion processing refers to a process of connecting, in the vertical direction of the image, places where the region of the steel chafer 18 located at the front side is segmented. Thereafter, the edge extraction unit 41e of the control device 41 defines the target region to the end portion of the steel chafer 18 located at the front side and identifies the position of the outer side edge 18b of the steel chafer 18 located at the front side or the ends of the steel cords 18c located at the front side and detects the locus of the positions of the outer side edge 18b in the tire circumferential direction (SB6). Thus, the image processing of the front side of the steel chafer 18 is completed. Note that by using dynamic binarization processing in the SB4 processing described above, the region can be more clearly differentiated than if typical binarization processing is used.

In addition, the inspection unit 41f of the control device 41 may inspect the arrangement of the steel cords 18c or the steel chafer 18 in the tire 1 on the basis of the detected position of the outer side edge 18b, i.e., the positions of the ends of the steel cords 18c of the steel chafer 18.

In such a manner, the tire inspection method of the present embodiment includes performing two dimensional Fourier transformation on a captured transmission electromagnetic wave image obtained from electromagnetic waves transmitting through:

a first region in the tire 1 (region of the front side of the steel chafer 18) in which a plurality of reinforcing wires (steel cords 18c) disposed in a reinforcing layer (steel chafer 18) of the tire 1 extends from first ends (steel chafer front side edge or the outer side edge 18b) at an incline in a first direction with respect to the tire width direction; and a second region (region of the back side of the steel chafer 18) in which the reinforcing wires (the steel cords 18c) extend at an incline in a second direction different from the first direction due to the reinforcing layer (steel chafer 18) being turned up. Thereafter, a first image component (the AND image) including the first ends of the reinforcing wires located in the first region is extracted from the two dimension Fourier transformation process result using a first spatial filter generated in accordance with the incline in the first direction. Additionally, a first processed image (transformed image) including the first ends located in the first region is acquired by performing inverse two dimension Fourier transformation on the extraction result of the first image component (AND image). By using this first processed image (transformed image), the positions of the first ends located in the captured image are identified. The position of the edge (steel chafer front side edge or the outer side edge 18b) of the reinforcing layer (steel chafer 18) in the tire is inspected on the basis of the identified positions of the first ends.

Next, the control device 41 performs image processing on the steel chafer 18 located at the back side (tire inner surface) (SA4).

Figure 8:
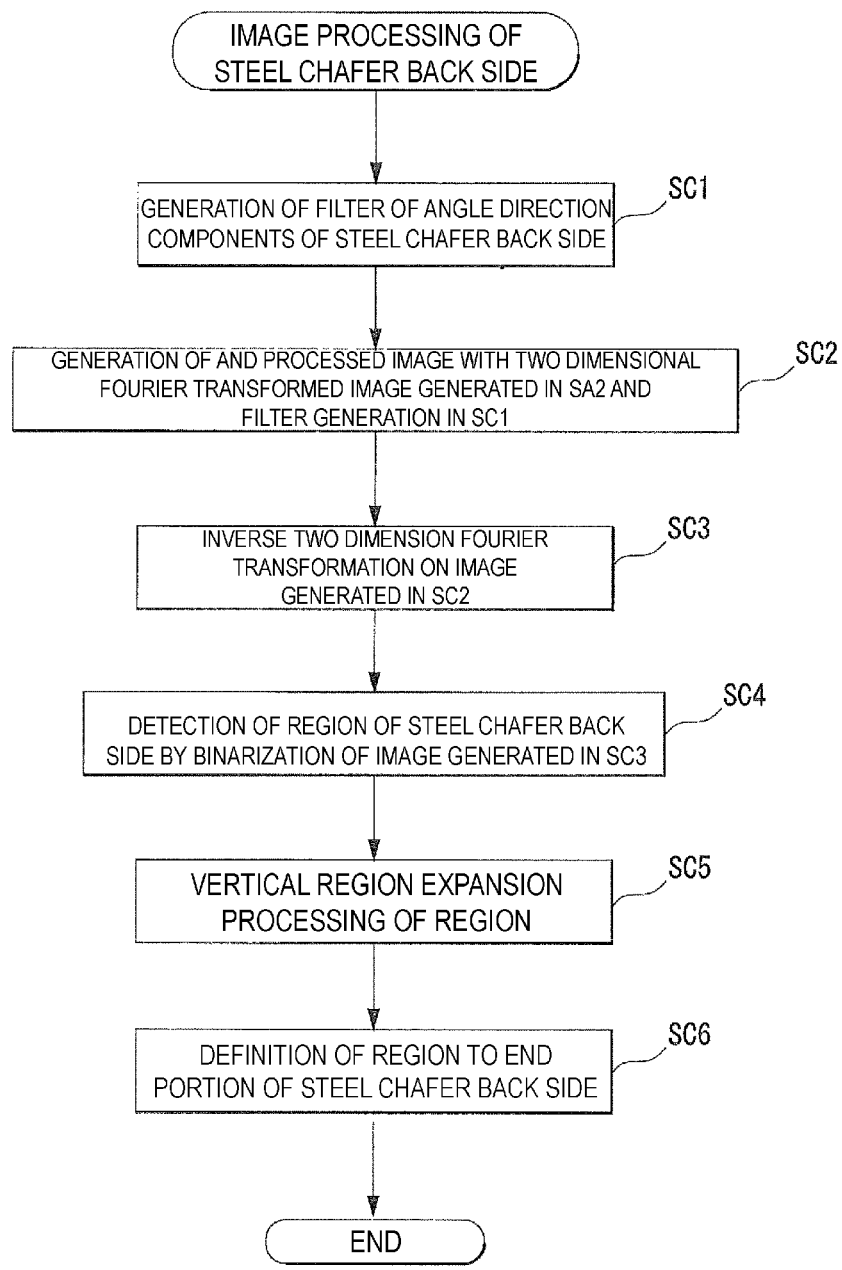
FIG. 8 is a flowchart for explaining the operation of the inspection device according to an embodiment of the present technology.

The image processing of the back side of the steel chafer 18 performed by the processed image acquisition unit 41b includes generating a spatial filter to extract only the steel cords 18c angle direction components of the steel chafer 18 located at the back side (SC1), as illustrated in FIG. 8. This spatial filter is generated in accordance with the incline of the steel cords 18c of the steel chafer 18 located at the back side. The angle of inclination of the steel cords 18c of the steel chafer 18 located at the back side are found by an inspector beforehand and the value is input into the control device 41 via the operation unit 43. Accordingly, the images of the steel cords 18c located at the back side are able to be separated from the images of the steel cords 18c located at the front side having a different angle of inclination and extracted.

The processed image acquisition unit 41b further performs an AND process with the two dimensional Fourier transformed image generated in the SA2 processing described above and the spatial filter generated in the SC1 processing described above and generates an AND image (SC2). Additionally, the processed image acquisition unit 41b performs inverse two dimension Fourier transformation of the AND image generated in the SC2 processing and generates a transformed image (SC3). This transformed image is an image in which the steel cords 18c of the steel chafer located at the back side are clearly shown.

Figure 11:
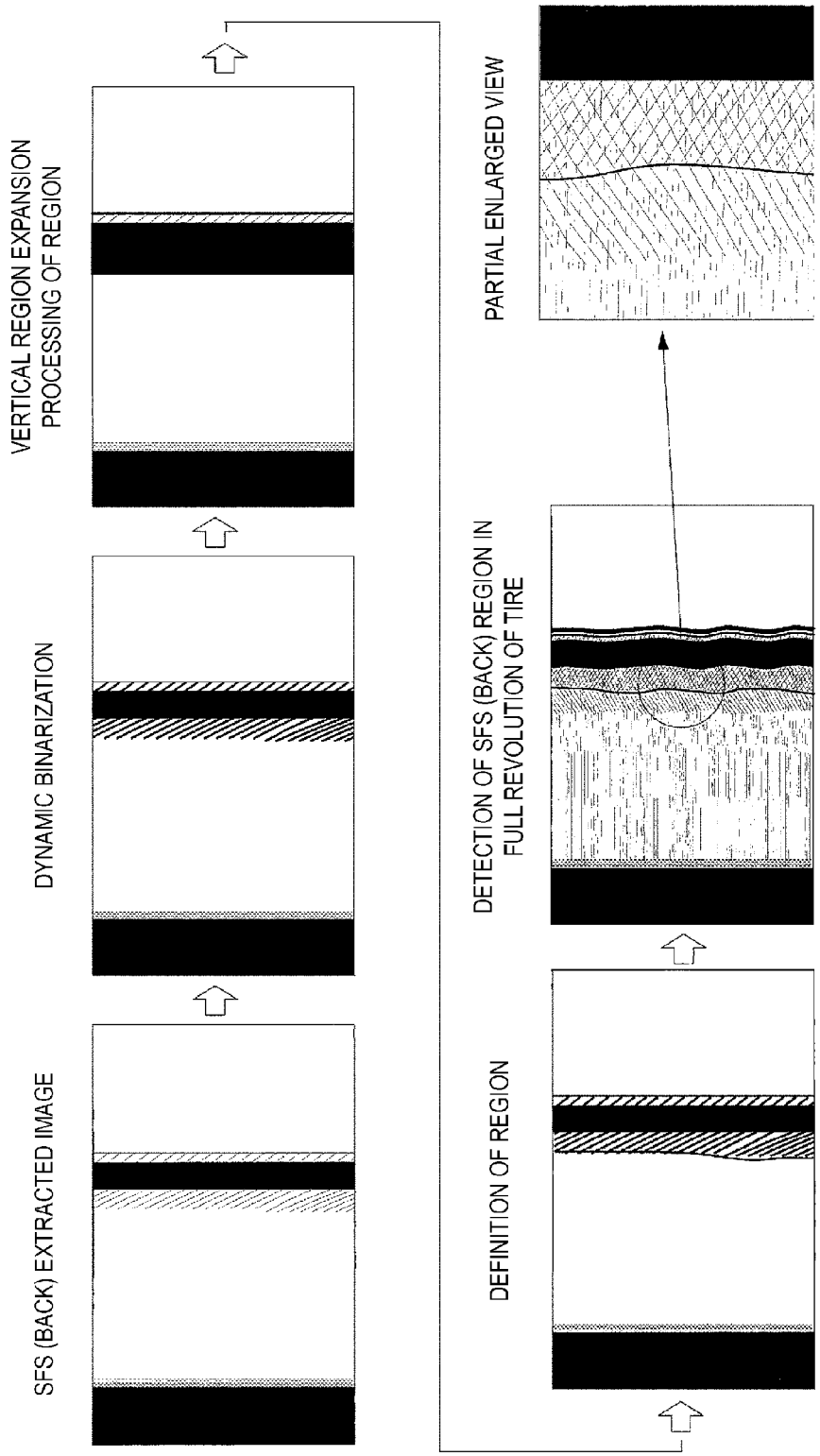
FIG. 11 is a diagram for explaining the steps involved in the image processing of detecting a back side edge of a steel chafer according to an embodiment of the present technology.

Next, the binarization processing unit 41d of the control device 41, as illustrated in FIG. 11, performs dynamic binarization processing on the transformed image generated in the SC3 processing and detects the region of the steel chafer 18 located at the back side (SC4) and further performs vertical region expansion processing (SC5). This vertical region expansion processing refers to a process of connecting, in the vertical direction of the image, places where the region of the steel chafer 18 located at the back side is segmented. Thereafter, the edge extraction unit 41e of the control device 41 defines the target region to the end portion of the steel chafer 18 located at the back side and identifies the position of the inner side edge 18a of the steel chafer 18 located at the back side and detects the locus of the positions of the inner side edge 18a in the tire circumferential direction (SC6). Thus, the image processing of the back side of the steel chafer 18 is completed. Note that by using dynamic binarization processing in the SC4 processing described above, the region can be more clearly differentiated than if typical binarization processing is used.

Accordingly, the inspection unit 41f of the control device 41 may inspect the arrangement of the steel cords 18c or the steel chafer 18 in the tire 1 on the basis of the position of the detected outer side edge or the outer side edge 18b and inner side edge 18a, i.e., both ends of the steel cords 18c of the steel chafer 18.

In such a manner, the reinforcing wires (steel cords 18c) of the present embodiment includes second ends (steel chafer back side edge 18a) located in the second region (the region at the back side of the steel chafer 18). In the present embodiment, a second image component (AND image) including the second ends (steel chafer back side edge 18a) of the reinforcing wires (steel cords 18c) located in the second region (the region at the back side of the steel chafer 18) is extracted from the two dimension Fourier transformation process result using a second spatial filter generated in accordance with the incline in a second direction. Additionally, a second processed image (transformed image) including the second ends (steel chafer back side edge 18a) located in the second region is acquired by performing inverse two dimension Fourier transformation on the extraction result of the second image component. By using this second processed image, the positions of the second ends located in the captured image are identified. In this case, the position in the tire 1 of the edge of the reinforcing layer (steel chafer 18) is preferably inspected on the basis of the positions of the second ends (steel chafer back side edge 18a) and the positions of the first ends (steel chafer front side edge or the outer side edge 18b).

Next, the working image generation unit 41c of the control device 41 performs differencing (SA5). Differencing includes generating a steel-chafer-component-removed Fourier transformed image, with the AND image components generated in the SB2 processing and the AND image components generated in the SC2 processing removed, from the two dimensional Fourier transformed image generated in the SA2 processing described above.

Thereafter, the working image generation unit 41c of the control device 41 performs inverse two dimension Fourier transformation of the steel-chafer-component-removed Fourier transformed image generated in the SA5 processing described above (SA6).

Next, the binarization processing unit 41d of the control device 41 detects a region where the carcass 14 is disposed by performing dynamic binarization processing (SA7) on the steel-chafer-component-removed image. Additionally, the edge extraction unit 41e defines the target region to the end portion of the carcass 14 and identifies the position of the carcass turned-up edge 14a and detects the locus of the positions of the carcass turned-up edge 14a in the tire circumferential direction (SA8). Note that by using dynamic binarization processing such as that performed in the SA7 processing described above, the region can be more clearly differentiated than if typical binarization processing is used.

Figure 12:
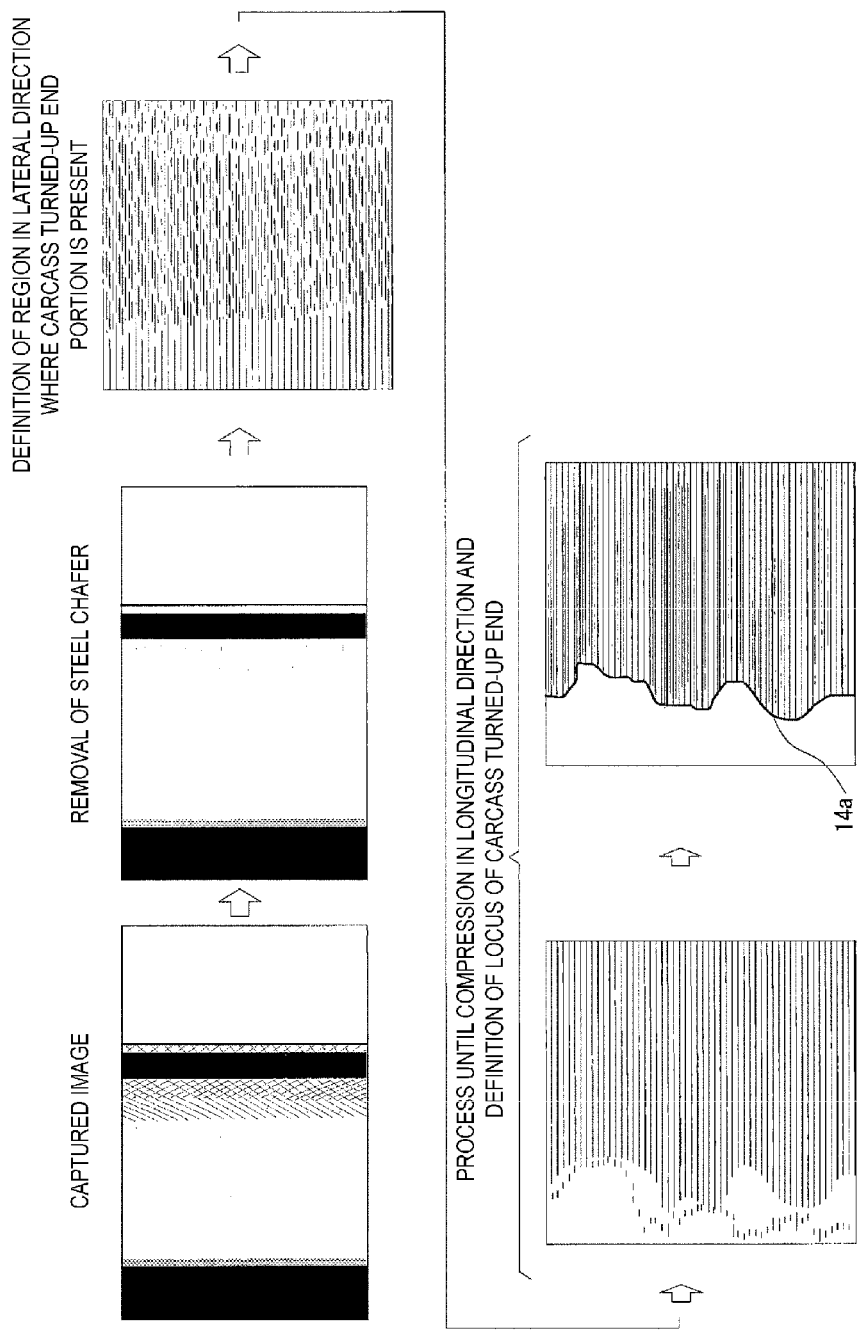
FIG. 12 is a diagram for explaining the steps involved in the image processing of detecting a carcass turned-up edge according to an embodiment of the present technology.

When the region where the carcass 14 is disposed and the locus of the carcass turned-up edge 14a are detected in the SA7 and SA8 processing described above, the steel chafer is removed from the captured image and this steel-chafer-component-removed image is defined to a region in the image lateral direction where the carcass turned-up edge is present, as illustrated in FIG. 12. Additionally, the image of a full revolution of the tire of the region where the carcass turned-up edge is present is compressed in the circumferential direction of the tire 1. The images from the captured image to the compressed image have gradation of 256 density levels. Via differences in gradation, the carcass turned-up edge is defined and the locus of the carcass turned-up edge 14a is detected.

Figure 13:
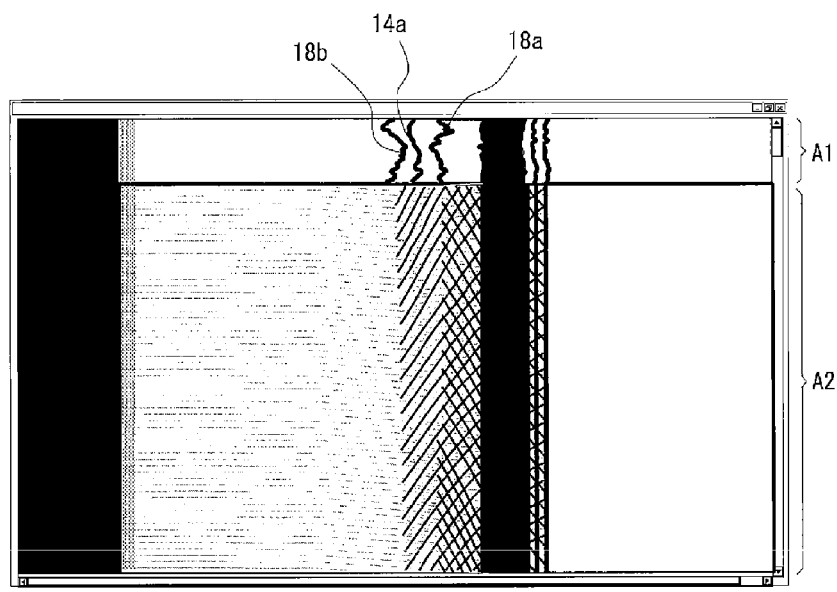
FIG. 13 is a diagram illustrating a display screen according to an embodiment of the present technology.

Next, the inspection unit 41f of the control device 41 inspects the arrangement of the carcass cords of the carcass 14 inside the tire 1, and specifically, determines whether the carcass 14 has a turned-up defect (SA9, SA10). In the case of the result of the determination being that the carcass 14 has a turned-up defect, then as illustrated in FIG. 13, a composite image (A1) of the compressed image of the captured image of the full revolution of the tire and the loci of the carcass turned-up edge 14a and inner side edge 18a and outer side edge 18b of the steel chafer is displayed on the liquid crystal display screen of the display unit 44. The display unit 44 also displays an uncompressed captured image (A2) on the liquid crystal display screen of the display unit 44. Additionally, information about these images and the acceptability determination result are stored in the exterior storage device 42 via instructions from the control device 41 (SA11). In the case of the result of the determination being that the carcass 14 has no turned-up defect, information about the image obtained via the processing described above and the acceptability determination results are stored in the exterior storage device 42 via instructions from the control device 41 (SA12). The processing described above is performed on bead portions 1a, 1a on both sides of the tire 1 in the tire width direction, thus completing the inspection of one tire 1.

In such a manner, in the present embodiment, a working image (steel-chafer-component-removed image) with the images of the reinforcing wires (steel cords 18c) in the first region (the region at the front side of the steel chafer 18) removed is preferably generated from the captured image using the captured image and the first processed image (transformed image obtained via inverse two dimension Fourier transformation). In such a case, additionally, the positions of third ends (turned-up ends of the carcass cords) of the skeleton wires (carcass cords) in the captured image are identified using this generated working image. On the basis of the identified positions of the third ends, the position of the edge of the skeleton member (carcass 14) in the tire is inspected.

Additionally, in the present embodiment, a working image (steel-chafer-component-removed image) with the images of the reinforcing wires in the first region (the region at the front side of the steel chafer 18) and the second region (region at the back side of the steel chafer 18) removed is preferably generated from the captured image using the captured image and the first processed image (transformed image obtained via inverse two dimension Fourier transformation of the Fourier transformed image extracted from the image of the steel cords 18c located at the front side) and the second processed image (transformed image obtained via inverse two dimension Fourier transformation of the Fourier transformed image extracted from the image of the steel cords 18c located at the back side). In such a case, additionally, the positions of the third ends (turned-up ends of the carcass cords) of the skeleton wires (carcass cords) in the captured image are identified using this generated working image (steel-chafer-component-removed image). On the basis of the identified positions of the third ends, the position of the edge of the skeleton member (carcass 14) is inspected.

Figure 14:
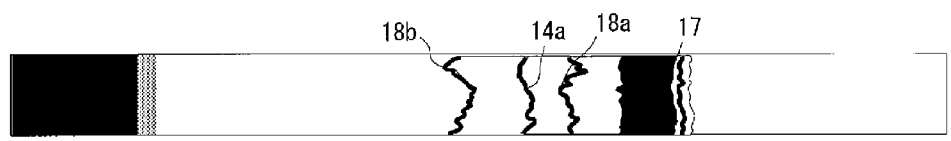
FIG. 14 is a diagram illustrating a compressed image of the captured image of a tire determined to be acceptable according to an embodiment of the present technology.

In the SA9 and SA10 determination processing described above of the present embodiment, the carcass turned-up edge 14a and the inner side edge 18a and outer side edge 18b of the steel chafer 18 are detected, as illustrated in FIG. 14, and if the distance from the bead 17 to the carcass turned-up edge 14a is greater than the distance from the bead 17 to the back side edge 18a of the steel chafer 18, which is located closest to the bead 17, then the tire is determined to be acceptable. Specifically, in the inspection of the position of the carcass turned-up edge of the carcass 14, inspection is performed all around in the tire circumferential direction, and when the positions of the ends of the carcass cords are closer to the turned-up position of the steel cords 18c than the positions of the ends at the front side of the steel cords 18c of the steel chafer 18 at all locations in the tire circumferential direction, the position of the carcass turned-up edge in the tire 1 is determined to be appropriate. Note that in the present embodiment, a tire is determined to be acceptable when the distance from the bead 17 to the carcass turned-up edge 14a is greater than the distance to the back side edge 18a of the steel chafer 18, however it is preferable to determine a position as acceptable when the carcass turned-up edge 14a is present between the edges 18a and 18b of the steel chafer 18. Specifically, in the inspection of the position of the carcass turned-up edge of the carcass 14, inspection is preferably performed all around in the tire circumferential direction, and when the positions of the ends of the carcass cords are between the positions of the ends at the front side of the steel cords 18c of the steel chafer 18 and the positions of the ends at the back side of the steel cords 18c of the steel chafer 18 at all locations in the tire circumferential direction, the position of the carcass turned-up edge of the carcass 14 in the tire 1 is determined to be appropriate.

As illustrated in FIG. 13, the liquid crystal display screen of the display unit 44 displays the composite image A1 of the compressed image of the captured image of a full revolution of tire and the loci of the carcass turned-up edge 14a and edge 18a and 18b of the steel chafer. By displaying the compressed image in such a manner, the state of the carcass turned-up edge 14a around the entire tire can be quickly verified. Additionally, verification of the section and kind of defect can be performed as the detailed image A2 is displayed and the full revolution of the tire can be viewed by scrolling through the screen. The screen can also change from the right side of the tire 1 to the left side by operating an operation button displayed on the screen.

Figure 15:
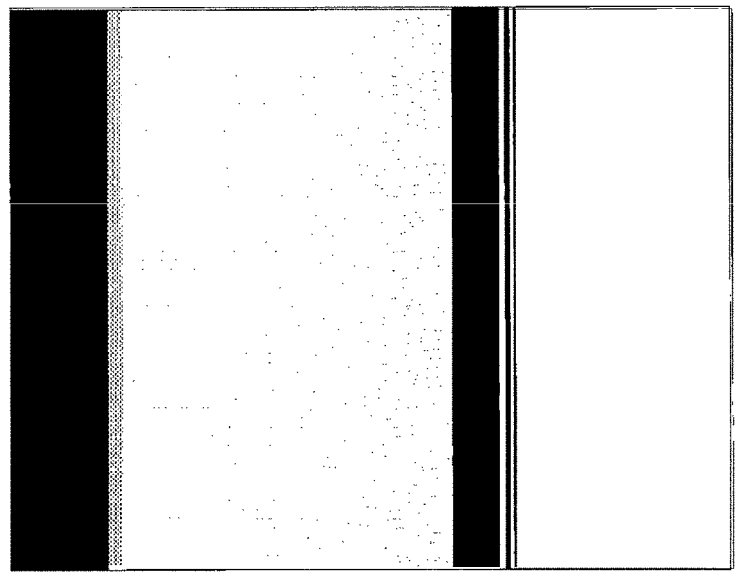
FIG. 15 is a diagram illustrating a captured image with steel cords removed and a compressed image thereof according to the present technology.
Figure 15:
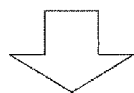
Figure 15:
Figure 16:
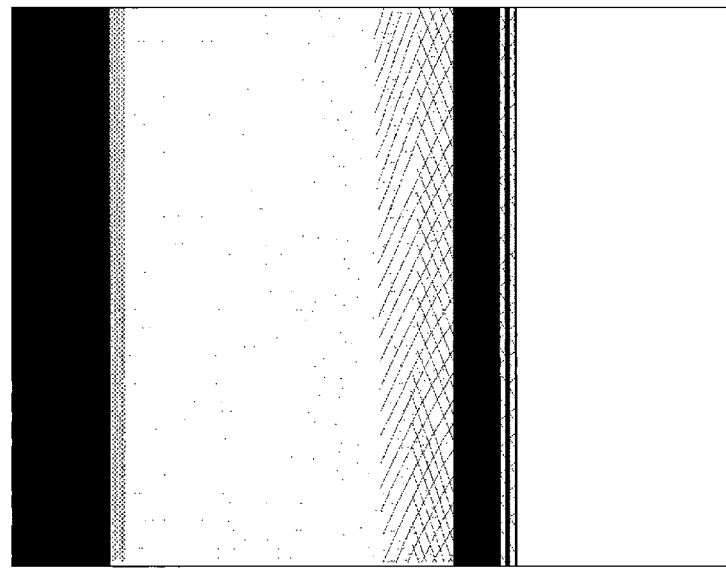
FIG. 16 is a diagram of a captured image without steel cords removed and a compressed image thereof according to the present technology.
Figure 16:
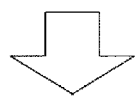
Figure 16:
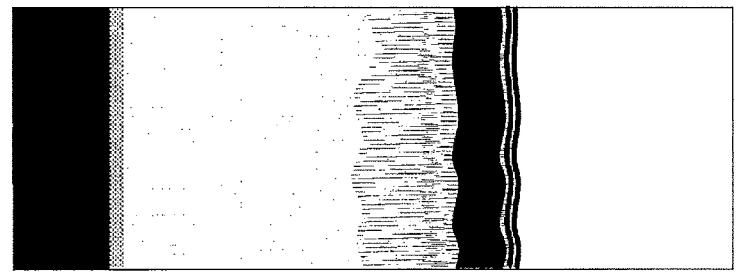

As in the embodiment described above, by generating an image of a full revolution of the tire 1, with the steel cords 18c of the steel chafer removed, compressed in the circumferential direction, the state of the carcass turned-up edge 14a can be quickly and easily verified compared to conventional means, as illustrated in FIG. 15. On the other hand, as seen in a conventional image (captured image) of a full revolution of the tire, without the steel cords 18c of the steel chafer removed, compressed in the circumferential direction, as illustrated in FIG. 16, the state of the carcass turned-up edge 14a is difficult to easily verify.

In the present embodiment, the steel chafer 18 is turned up at the bead portion 1a. As a result, the angle of inclination of the steel cords 18c with respect to the tire width direction changes from positive to negative while having the same absolute value. However, the absolute value of the angle of inclination may change provided that the images of the steel cords 18c can be extracted using the spatial filter described above in accordance with the angle of inclination.

Note that as in the present embodiment, the positions of the front side ends and back side ends of the steel cords 18c of the steel chafer 18 and the front side ends of the carcass cords are preferably identified as positions on a locus of a full revolution of the tire along the tire circumferential direction.

According to the tire inspection method and inspection device of the present embodiment described above, the edge loci 18a, 18b of the steel chafer and the locus of the carcass turned-up edge 14a can be automatically extracted from the image of the full revolution of the tire. Thus, the determination of a carcass turned-up defect can be performed with greater accuracy than if performed by an inspector and determination with 100% reproducibility and repeatability is possible. In addition, because visual observation of an image by an inspector becomes unnecessary, the tire rotation speed can be set high, thus shortening the cycle time.

The present technology relates to a tire inspection method capable of inspecting for acceptability of the position of a turned-up edge of a carcass efficiently and accurately using a transmission electromagnetic wave image captured by irradiating a tire with electromagnetic waves, and a device therefor. The determination of a carcass turned-up defect can be performed with greater accuracy and in less time than when performed by an inspector and 100% reproducibility and repeatability is possible. In addition, because visual observation of an image by an inspector becomes unnecessary, the tire rotation speed upon image capturing can be set high, thus shortening the cycle time.

The invention claimed is:

1. A tire inspection method comprising the steps of:
performing two dimension Fourier transformation on a captured transmission electromagnetic wave image obtained from electromagnetic waves transmitting through:
  a first region in a tire in which a plurality of reinforcing wires disposed in a reinforcing layer of the tire extends from first ends of the reinforcing wires at an incline in a first direction with respect to a tire width direction, and
  a second region in the tire in which the reinforcing wires extend at an incline in a second direction different from the first direction due to the reinforcing layer being turned up,
  wherein the tire comprises a layer-like skeleton member including a plurality of tire skeleton wires disposed in the first region and the second region, the tire skeleton wires extending in a third direction different from the first direction and the second direction and including third ends located in the first region, and wherein the captured image includes images of the reinforcing wires and the skeleton wires;
extracting a first image component including the first ends of the reinforcing wires located in the first region from a process result of the two dimension Fourier transformation using a first spatial filter generated in accordance with the incline in the first direction;
acquiring a first processed image including the first ends located in the first region by performing inverse two dimension Fourier transformation on an extraction result of the first image component;
generating a working image from the captured image by removing the images of the reinforcing wires located in the first region using the captured image and the first processed image;
identifying positions of the first ends in the captured image using the first processed image;
identifying positions of the third ends of the skeleton wires in the captured image using the working image;
inspecting a position of an edge of the reinforcing layer in the tire on the basis of the positions of the first ends; and
inspecting a position of an edge of the skeleton member in the tire on the basis of the identified positions of the third ends.

2. The tire inspection method according to claim 1, wherein the reinforcing wires include second ends located in the second region; and
further comprising the steps of:
extracting a second image component including the second ends of the reinforcing wires located in the second region from a process result of the two dimension Fourier transformation using a second spatial filter generated in accordance with the incline in the second direction,
acquiring a second processed image including the second ends located in the second region by performing inverse two dimension Fourier transformation on an extraction result of the second image component, and
identifying positions of the second ends in the captured image using the second processed image, wherein
upon the inspection, the position of the edge of the reinforcing layer in the tire is inspected on the basis of the positions of the second ends and the first ends.

3. The tire inspection method according to claim 2, wherein
the tire comprises a layer-like skeleton member including a plurality of tire skeleton wires disposed in the first region and the second region, the tire skeleton wires extending in a third direction different from the first direction and the second direction and including third ends located in the first region;
the captured image includes images of the reinforcing wires and the skeleton wires; and further comprising the steps of:
generating a working image from the captured image by removing the images of the reinforcing wires located in the first region and the second region using the captured image, the first processed image, and the second processed image,
identifying positions of the third ends of the skeleton wires in the captured image using the working image, and
inspecting a position of an edge of the skeleton member on the basis of the identified positions of the third ends.

4. The tire inspection method according to claim 1, wherein the positions of the third ends are identified on the basis of an image generated by performing dynamic binarization processing on the working image.

5. The tire inspection method according to claim 1, wherein
the position of the edge of the skeleton member is inspected all around in a tire circumferential direction, and
if the positions of the third ends are closer to a turned-up position of the reinforcing wires than the position of the first ends at all locations in the tire circumferential direction, the position of the edge of the skeleton member in the tire is determined to be appropriate.

6. The tire inspection method according to claim 1, wherein
the position of the edge of the skeleton member is inspected all around in the tire circumferential direction, and
if the positions of the third ends are between the positions of the first ends and the positions of the second ends at all locations in the tire circumferential direction, the position of the edge of the skeleton member in the tire is determined to be appropriate.

7. The tire inspection method according to claim 1, wherein the positions of the first ends, the second ends, and the third ends are identified as positions on corresponding loci of a full revolution of the tire along the tire circumferential direction.

8. The tire inspection method according to claim 1, further comprising the step of:
displaying a composite image of:
an image of a full revolution in the tire circumferential direction of the captured image compressed in the tire circumferential direction, and
loci in a full revolution of the tire of the positions of the first ends of the reinforcing wires, positions of the second ends of the reinforcing wires, and the positions of the third ends of the skeleton wires.

9. The tire inspection method according to claim 1, further comprising the step of displaying the captured image.

10. The tire inspection method according to claim 1, wherein the reinforcing layer is a steel chafer disposed at the bead portion, the steel chafer including steel cords.

11. The tire inspection method according to claim 1, wherein the skeleton member is a carcass turned up at the bead portion.

12. A tire inspection device comprising:
a two dimension Fourier transformation unit configured to perform two dimension Fourier transformation on a captured transmission electromagnetic wave image obtained from electromagnetic waves transmitting through:
a first region in a tire in which a plurality of reinforcing wires disposed in a reinforcing layer of the tire extends from first ends of the reinforcing wires at an incline in a first direction with respect to a tire width direction, and
a second region in the tire in which the reinforcing wires extend at an incline in a second direction different from the first direction due to the reinforcing layer being turned up,
wherein the tire comprises a layer-like skeleton member including a plurality of tire skeleton wires disposed in the first region and the second region, the tire skeleton wires extending in a third direction different from the first direction and the second direction and including third ends located in the first region and wherein the captured image includes images of the reinforcing wires and the skeleton wires;
a processed image acquisition unit configured to
extract a first image component including the first ends of the reinforcing wires located in the first region from a process result of the two dimension Fourier transformation using a first spatial filter generated in accordance with the incline in the first direction, and
acquire a first processed image including the first ends located in the first region by performing inverse two dimension Fourier transformation on an extraction result of the first image component;
a working image generation unit configured to generate a working image from the captured image by removing the images of the reinforcing wires located in the first region using the captured image and the first processed image;
an edge extraction unit configured to identify positions of the first ends in the captured image using the first processed image, and to identify positions of the third ends of the skeleton wires in the captured image using the working image; and
an inspection unit configured to inspect a position of an edge of the reinforcing layer in the tire on the basis of the positions of the first ends, and to inspect a position of an edge of the skeleton member in the tire on the basis of the identified positions of the third ends.

13. The tire inspection device according to claim 12, wherein
the reinforcing wires include second ends located in the second region;
the processed image acquisition unit is configured to
extract a second image component including the second ends of the reinforcing wires located in the second region from a process result of the two dimension Fourier transformation using a second spatial filter generated in accordance with the incline in the second direction of the reinforcing wires, to
acquire a second processed image including the second ends located in the second region by performing inverse two dimension Fourier transformation on an extraction result of the second image component;
the edge extraction unit is configured to identify positions of the second ends in the captured image using the second processed image; and
the inspection unit is configured to inspect the position of the edge of the reinforcing layer in the tire on the basis of the positions of the second ends and the first ends.

14. The tire inspection device according to claim 13, wherein
the tire comprises a layer-like skeleton member including a plurality of tire skeleton wires disposed in the first region and the second region, the tire skeleton wires extending in a third direction different from the first direction and the second direction and including third ends located in the first region;
the captured image includes images of the reinforcing wires and the skeleton wires;
the tire inspection device comprises a working image generation unit configured to generate a working image from the captured image by removing the images of the reinforcing wires located in the first region and the second region using the captured image, the first processed image, and the second processed image;
the edge extraction unit is configured to identify positions of the third ends of the skeleton wires in the captured image using the working image; and
the inspection unit is configured to inspect the position of the edge of the skeleton member in the tire on the basis of the identified positions of the third ends.

15. The tire inspection device according to claim 12, further comprising:
a binarization unit configured to perform dynamic binarization processing on the working image, and wherein
the edge extraction unit is configured to identify the positions of the third ends on the basis of the working image on which the dynamic binarization processing is performed.

16. The tire inspection device according to claim 12, wherein
the inspection unit determines the position of the edge of the skeleton member in the tire to be appropriate if the positions of the third ends are closer to a turned-up position of the reinforcing wires than the positions of the first ends at all locations in the tire circumferential direction.

17. The tire inspection device according to claim 12, wherein the inspection unit determines the position of the edge of the skeleton member in the tire to be appropriate if the positions of the third ends are between the positions of the first ends and the positions of the second ends at all locations in the tire circumferential direction.

18. The tire inspection device according to claim 12, wherein the edge extraction unit identifies the positions of the first ends, the second ends, and the third ends as positions on corresponding loci of a full revolution of the tire along the tire circumferential direction.

19. The tire inspection device according to claim 12, further comprising a display unit configured to display a composite image of:
   an image of a full revolution in the tire circumferential direction of the captured image compressed in the tire circumferential direction, and
   loci in a full revolution of the tire of the positions of the first ends of the reinforcing wires, positions of the second ends of the reinforcing wires, and the positions of the third ends of the skeleton wires.

20. The tire inspection device according to claim 12, further comprising a display unit configured to display the captured image.

* * * * *